(12) United States Patent
MacAdam et al.

(10) Patent No.: US 8,275,452 B2
(45) Date of Patent: Sep. 25, 2012

(54) RAPID 3D MAPPING USING MULTIELECTRODE POSITION DATA

(75) Inventors: David P. MacAdam, Millbury, MA (US); Minoru Mashimo, Windham, NH (US); Pawel Kuklik, Warsaw (PL); Bruce Stoller, Milford, NH (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 13/209,232

(22) Filed: Aug. 12, 2011

(65) Prior Publication Data

US 2012/0035488 A1  Feb. 9, 2012

Related U.S. Application Data

(62) Division of application No. 12/117,654, filed on May 8, 2008, now Pat. No. 8,224,432.

(60) Provisional application No. 60/916,749, filed on May 8, 2007.

(51) Int. Cl.
*A61B 5/04* (2006.01)

(52) U.S. Cl. .................................. 600/523

(58) Field of Classification Search .......... 600/509, 600/523
See application file for complete search history.

(56) References Cited

U.S. PATENT DOCUMENTS

| | | |
|---|---|---|
| 5,687,737 A | 11/1997 | Branham et al. |
| 2006/0241518 A1 | 10/2006 | Boese et al. |
| 2007/0073179 A1 | 3/2007 | Afonso et al. |
| 2008/0009758 A1 | 1/2008 | Voth |

*Primary Examiner* — Brian T Gedeon
(74) *Attorney, Agent, or Firm* — Leason Ellis LLP

(57) ABSTRACT

An electrophysiology (EP) system includes an interface for operator-interaction with the results of code executing therein. A template model can have channels positioned or repositioned thereupon by the user to define a set-up useful in rapid catheter positioning. Mapping operations can be performed without the requirement for precise catheter location determinations. A map module coordinates EP data associated with each selected channel and its associated position on the template model to provide this result, and can update the resulting map in the event that the channel or location is changed. Messaging and other dynamic features enable synchronized presentation of a myriad of EP data. Additional systems and methods are disclosed herein.

18 Claims, 8 Drawing Sheets

Pre-ablation CS pacing
(9 data points)

Pre-ablation CS pacing
(7 data points)

RAPID 3D MAPPING USING MULTIELECTRODE POSITION DATA

This application is a divisional of U.S. patent application Ser. No. 12/117,654, now U.S. Pat. No. 8,224,432 filed May 8, 2008, which claims the benefit of priority under 35 U.S.C. Section 119(e) of U.S. Provisional Application Serial No. 60/916,749, filed May 8, 2007, which are hereby incorporated by reference in their entireties.

FIELD OF THE INVENTION

This invention is directed to improvements in electrophysiology (EP) systems and procedures including software that assists in data management across various systems in the EP laboratory including systems that provide electrogram capture, electrogram analysis, fluoroscopic display, and that permit, among other things, 3D colorized mapping of captured and analyzed data to provide an electrophysiologist with information in a form that assists in his or her diagnosis or documenting that an EP issue has been resolved.

BACKGROUND OF THE INVENTION

Many cardiac arrhythmias are caused by conduction defects that interfere with the propagation of normal electrical signals within the heart. The method adopted to treat arrhythmia is dependent on the nature and position of the underling conduction defect. Thus, electrophysiological mapping plays an important role in measuring the electrical activity of the heart. These techniques often require specialized equipment to locate the position of catheters in physical space and reconstructing the shape of the chamber from multiple site recordings. It would be desirable to provide 3D mapping without such equipment.

State of the Art 3D mapping systems use magnetic fields, electrical fields or ultrasound to localize catheters. The main disadvantage of these systems is the prohibitive cost involved with the equipment and the need for both a conventional EP recording system and a separate 3D mapping/localization system. While manual positioning is not as accurate as current technologies, it is significantly more cost effective than conventional EP mapping systems and can be performed more rapidly.

It remains necessary to locate a target (active) site if an arrhythmia is to be terminated. A number of catheter locating systems are known in the art, but each introduces components and complexity to EP procedures. EP operators, however, are usually quite capable of piloting an EP catheter to a desired site within a patient's vasculature, particularly with fluoroscopic assistance. A difficulty remains, even if the location of the catheter is estimated based on fluorscopic guidance, in matching indwelling EP electrodes to sites on a cardiac model. This problem is all the more difficult when the model is rendered in 3D.

In part, the operator has data captured by a variety of systems. For example, electrogram channels monitor signals from indwelling electrodes, such as intracardiac electrodes and reference electrodes, and that information has to be coordinated with an anatomical (e.g., cardiac) model. Fluoroscopic images of the anatomy generally have no connection to other systems in the EP lab, and so piloting a catheter that lacks a locating system is done as a parallel, distinct part of the EP procedure. Cardiac mapping, therefore, has required great effort at a time when the operator's attention needs to focus on the patient or in labs where cost is an impediment and a highly trained technician is not available to operate a complex 3D mapping system.

The present invention addresses one or more of these problems.

SUMMARY OF THE INVENTION

In accordance with one aspect of the present invention, an electrophysiology (EP) system for use by an operator is provided. The system includes an interface having an output device comprising a display and an input device comprising a control panel, a processor, and code executing in the processor. The code comprises at least a first routine that is operative to respond to user-interaction through the control panel. Among other functionality, the code provides a selection of channels having associated EP data that is viewable on the display, informs a map module of any selections made among the selection of channels so as to link any EP data associated with any selections to the map module, permits positioning of the channels at respective locations on a template model to define a set-up, and saves the set-up for use in one or more procedures. The code is further operative to calculate values as a function of both the EP data and any positioning of the channels to said respective locations.

In further, optional arrangements of the system described above, the code can be arranged to: permit positioning of the channels through a dragging operation performed through the interface; display the EP data associated with any selections of channels at any of said respective locations on the template model in accordance with a color scale using interpolation calculations; permit user-positioning of a boundary zone along a portion of a surface of the template model which can be used to exclude the portion of the surface of the template model from any interpolation calculations; permit a region of the surface of the template model to be selected and transformed into a transparent region; to capture images (e.g., a fluoroscopic image) as part of a record of a data capture event; and to exchange messages that permit synchronization of displays of electrocardiogram waveforms and other EP equipment.

In accordance with a further aspect of the present invention, an electrophysiology system useful for conducting an EP data capture procedure is provided. This system comprises a computer having a memory, a processor, and computer code executing in the processor and operable through a user-interface. A display is communicatively coupled to the computer. A template model of a surface of a heart is stored in the memory and selectable via the user-interface for display on the display. At least one set-up is establishable using the user-interface, the set-up comprising a plurality of particular locations on the surface of the template model at which a corresponding plurality of ECG channels are associable. A connection to an EP system receives the EP data from the plurality of the ECG channels. The computer code in this system is operative to impart a color coding across the surface of the template model as a function of the set-up and as a further function of any EP data received through the connection.

In further, optional arrangements of the system described in the paragraph immediately above, color coding comprises a spectrum of colors on a color scale in which a color is assigned to each particular location and wherein the computer code imparts colors from the color scale across the surface of the template model by interpolation. Also, a user-positionable boundary zone can be stored in the memory as part of the template model, with the boundary zone being used by the computer code to exclude a portion of the surface of the template model from the interpolation of colors. Optionally, the particular locations on the surface of the template model that comprise the set-up are repositionable.

In accordance with yet a further aspect of the present invention, an electrophysiology system is provided which has an interface comprising an output device comprising a display and an input device comprising a control panel. A processor has code executing therein that comprises at least a first routine operative to respond to user-interaction through the interface to reposition one or more markers presented on the display and to automatically compute EP data values as a function of the repositioning of the one or more markers. The interface provided in accordance with this particular aspect of the invention optionally provides a map having a surface depicting the EP data values thereupon. When a map is provided, the code can respond to the user-interaction by providing updates to the map. An event log can be provided through the interface as well, and the code can respond to certain user-interactions with updates being made to the event log.

In yet another aspect of the present invention, a computer-assisted method for guiding an operator in a placement of indwelling electrodes is disclosed. In the disclosed method, a template model of a heart is provided on a display connected to the computer. A "set-up" is included within the display of the template model of the heart in which a plurality of locations are marked on the template model as locations that correspond to a respective plurality of ECG channels. A catheter having a proximal end and a distal end that supports multiple electrodes is advanced into the heart of a patient, and the multiple electrodes are piloted (e.g., navigated) into an orientation that generally coincides with the set-up on the template model surface by manipulating the proximal end of the catheter. EP data is captured at the piloted locations onto electrogram channels associated with the respective ones of the multiple electrodes. In this way, the catheter is navigated free of a precision navigation device.

In further, optional aspects of the foregoing method, a set of data points is stored wherein each data point has a location that corresponds to a respective location of one of the points in the set-up and a value that corresponds to the EP data on that channel. Also, the set-up included in the display of the template model can be pre-defined or constructed by the user using controls provided on the EP system interface. Furthermore, as Ep data is captured, portions of the template model can be caused to have an opacity that is greater than portions of the template model in which there has been less or no mapping of EP data.

These and other aspects, features, and steps can be better appreciated from the following discussion of certain embodiments and the accompanying drawing figures.

DETAILED DESCRIPTION OF CERTAIN EMBODIMENTS

By way of overview and introduction, the present invention concerns 3-D mapping of cardiac data obtained during the course of an electrophysiology procedure. A segmented model of a heart can be acquired from a CT scan of a patient, or from a library of "typical" anatomies for patients having like characteristics. A software-based system populates the segmented model with data points that define a 3D map. The EP data at each data point is extracted from electrograms captured for one or more channels. The EP data for each channel is associated with an electrode, and the location of that electrode and hence the data point on the model can be defined on the map in several ways that simplify the equipment and operative steps that are required to construct a meaningful map, as described below.

In particular, and still by way of overview, the locations of one or more channels can be defined on a template model of a heart and stored for recall and use in a number of procedures. A "set-up" is a position of a single-pole or multipole catheter at which data is to be collected for a given procedure (VT mapping, typical right atrial flutter, etc.). A defined set-up is particularly desirable when using a multi-electrode catheter such as a twenty pole catheter because the operator can pilot the catheter into the orientation indicated on the template and then capture EP data without being concerned with the precise location of any of the particular electrodes. In this regard, it can be appreciated that a set-up can be pre-defined by the software or user defined. In either case, the set-up can be selected through controls on the EP system (e.g., the Lab System Pro 2.4 available from C. R. Bard, Inc. of Murray Hill, N.J.) which causes pre-positioned points to display within the segmented model. These pre-positioned points can become data points once the operator confirms, e.g., with fluoroscopic assistance, that the catheter has been guided into a position that approximates the catheter set-up. Once the desired position and orientation has been confirmed by the operator, using his professional skill and judgment, the data can be captured (recorded) by transferring the electrogram information from each channel to the particular point in the set-up that is associated with that electrogram data.

Figure 1:
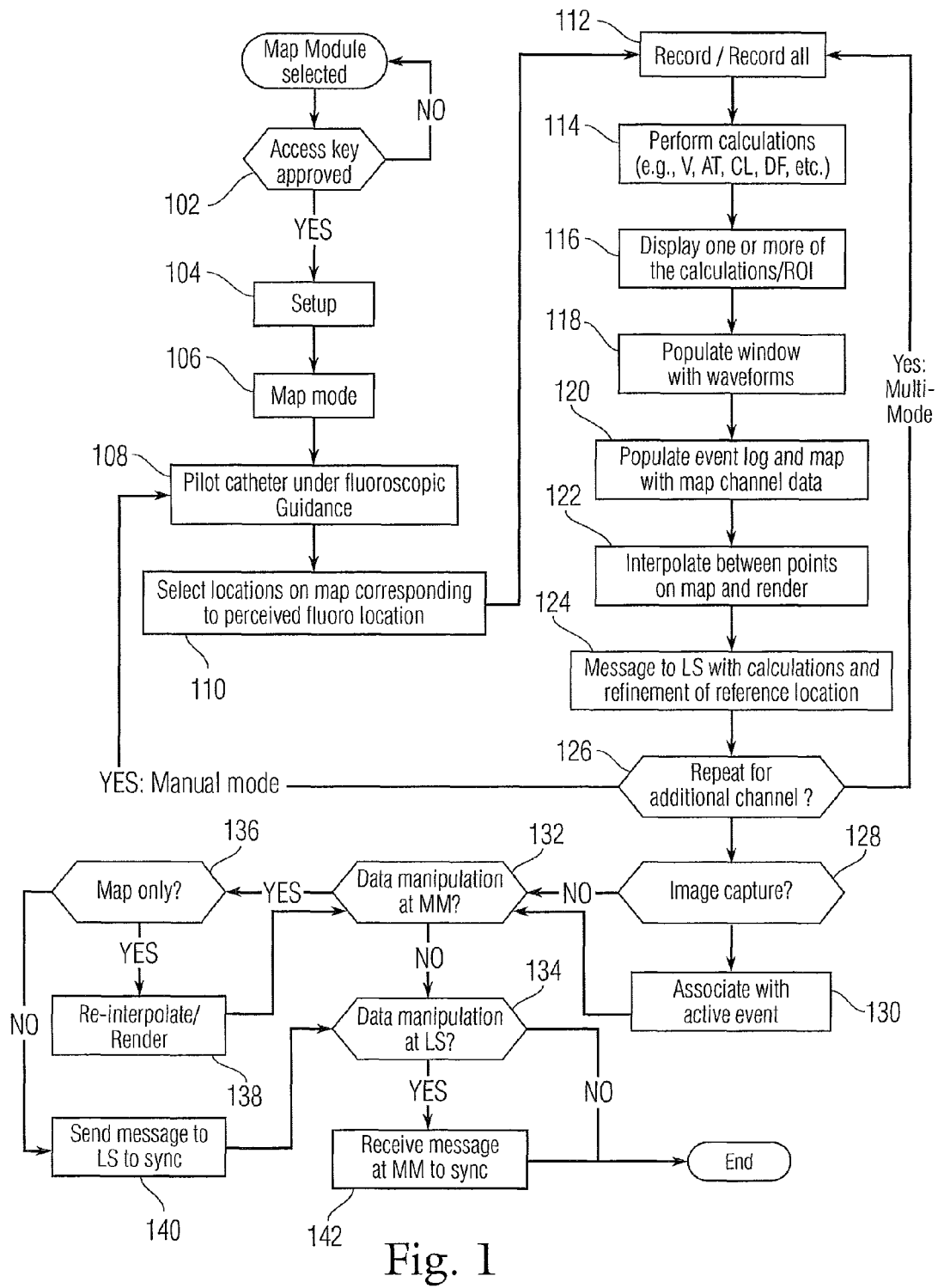
FIG. 1 is a flow diagram concerning user interaction through a software-based user interface with a map module.

Referring now to FIG. 1 a software module that operates in conjunction with an electrophysiology ("EP") laboratory system, such as the aforementioned Lab System Pro ("LS Pro"), provides functionality that enables the user to rapidly apply three cardiac data points captured during an EP procedure onto a 3-D anatomical model of the heart.

At block 102, an optional test is performed to ensure that the operator is using an authorized catheter or otherwise has valid access to the map module functionality. At block 102, a test is made to determine whether an access key entered through the interface is valid. Until a valid key is entered into the module, the operator is not granted access to the map module's functionality. As can be understood, a module can be implemented without the access key test.

Once the map module has been activated, a basic usage scenario includes "setup" followed by the repeated steps of positioning the electrogram, determining a mapping channel location on the anatomy in the 3D View, and capturing data points. Generally, setup includes opening or establishing a patient record for a session.

Figure 2:
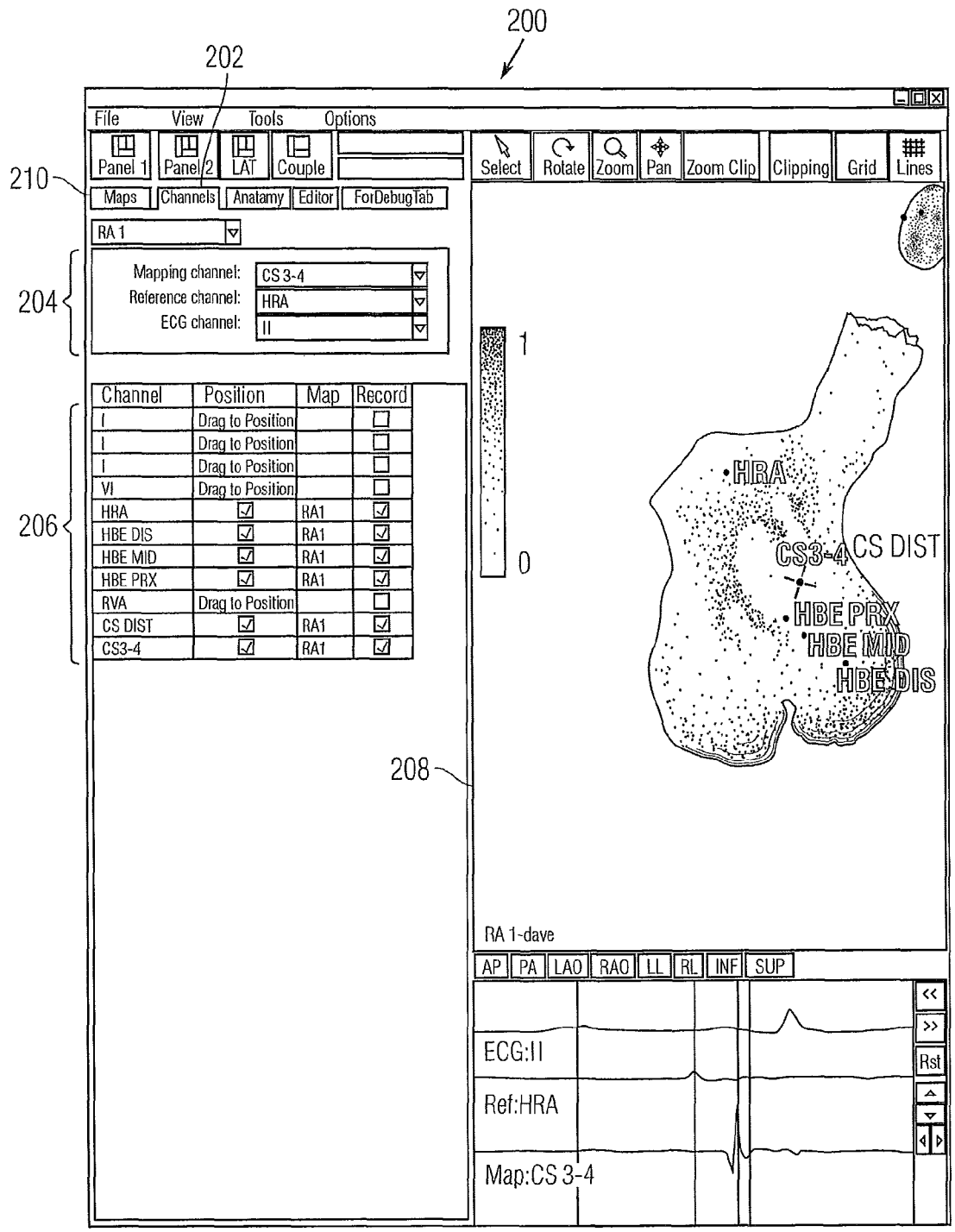
FIG. 2 illustrates an embodiment of certain panels that can be provided by the user interface for setting up a 3D map configuration.

At block 104, the software is configured in order to be able to render cardiac data onto a three dimensional surface. The configuration steps include steps taken through the map module itself, as well as steps taken on the EP system. Referring briefly to FIG. 2, a channel setup page 200 of the map module is shown in exemplary form. This page is accessed by selecting an appropriate tab such as tab 202 or using any other control that can be provided for such selection through the user interface. The channel setup page enables the user to define which channel is for mapping, which channel is to be the reference channel and which ECG channel is to be displayed in conjunction with the other traces. These selections are made in region 204 of the channel setup page, preferably with prompts provided by a pull-down selection list showing the active channels that are available for selection. Preferably the EP system informs the map module of the active channels through conventional messaging. The active channels should correspond to the electrodes that have been affixed or inserted within the anatomy of a patient or that were active during the EP procedure whose electrograms are being provided to the map module (that is, when the map module is being used after the EP procedure). Region 206 shows the set of available channels in an exemplary setup. Among the available channels, six have been designated on a segmented model of the heart, as shown in panel 208. In particular, the six channels which have been designated on the heart are the three HBE channels, the HRA channel, and the two CS channels. The remaining channels can be selected by dragging the channels from the left panel 206 to a location on the heart image within the anatomy panel 208 that generally corresponds to its location in the patient. In other words, the user interface permits interaction with the heart template and a selection of channels such that the channels can be positioned and repositioned using a mouse or similar input device.

Each of the channels available for selection has an associated electrogram that is viewable on the EP system. Even if a channel is available for selection, an operator may elect to deselect or not select a given channel from the template based on clinical conditions. For example, if an undesirably noisy signal is being read on a particular channel, then that channel might be deselected or not selected, and another channel dragged to the template for use in a current procedure or in a review mode, as discussed below. If the voltage on one of the channels is low, the user interface of the map module allows editing of the anatomy so as to exclude certain tissue from the mathematical models. For example, the operator can paint that location of low voltage reading as a "scar" and thereby preclude any further measurements at that electrode position. The scar is added to the model by a click-and-drag operation in which tissue on the model at the locations of the input device are assigned a color outside of the color scale that indicates local activation or any other parameter of interest, such as grey, black or brown.

Also, the initially selected channels appear as grey or uncolored markers (e.g., spheres) on the segmented model because those positions are not associated with any EP data as of yet. Once the physician navigates the catheter to those positions within the heart, then the model can be updated by recording the EP data and associating that data with the designated positions on the model.

In FIG. 2, a particular CT cardiac image has been selected, and this image can be an image of the patient or an image taken from a library of cardiac CT images. The CT image shown in panel 208 comprises a segmented model of a heart as understood by those of skill in the art, which provides a hollow surface that approximates the internal surface of an actual heart. Once a desired set of channels has been positioned on a particular heart, it can be saved as a template or setup for use in a present procedure, or in a future procedure. For example, a template can be saved under the title "right isthmus dependent flutter setup," and that template can be used for more than one patient who generally fits the criteria for the particular segmented model that has been selected (e.g., a model of a normal heart of a 160 lb Male) and saved in that template. As well, multiple templates can be called up and combined, for example, to map multiple portions or chambers of the heart.

In addition, and as discussed with regard to FIGS. 8A and 8B below, the saved templates can be saved again after data has been acquired. As one example, a particular template can be saved as a pre-ablation and a post-ablation map with the electrodes at particular positions in both maps.

In the event that the user wishes to locate a channel elsewhere on the heart, the user can drag the original location of the channel to a new location, by interacting with the channel markers displayed within the pane 208.

Figure 4:
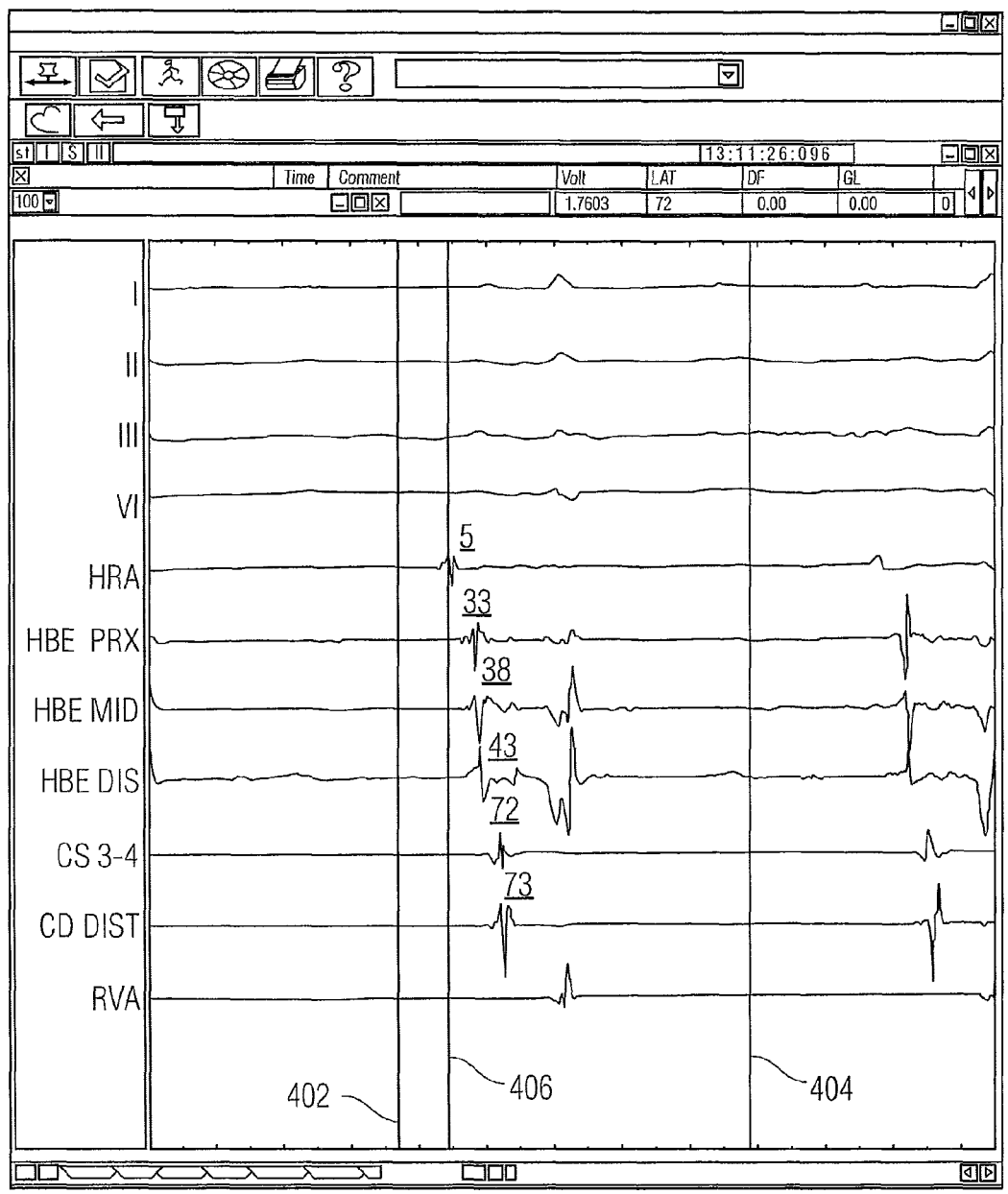
FIG. 4 illustrates an embodiment of a user interface associated with an EP system for capturing and presenting electrograms for multiple channels, which further includes interactive graphical markers that are positionable and repositionable by a user through the user interface.

The setup (block 104) also requires that a region of interest be specified, generally, a region that spans one beat. (In this respect, the region of interest can be, but is not limited to being, synonymous with a beat of interest.) Also, a reference marker must be established at a particular location on the electrogram waveform of the selected reference channel. Both of these settings can be done through a EP system such as the LS Pro. Turn briefly to FIG. 4, a region of interest across one beat of the heart can be identified by clicking and/or dragging region of interest end point markers 402, 404 as shown in FIG. 4. The region of interest markers 402, 404 are graphical objects that can be manipulated and have their values updated by dragging and then releasing them within an active window. This might be necessary, for example, if the cardiac rhythm changes during the course of an EP procedure, and can be done without specifying any particular number of milliseconds before or after a beat as required in prior-art trial and error systems. The user can review the beat across all of the channels on the EP system and move the markers through interaction with the GUI. The reference marker 406 is identified by clicking on a desired point of a reference channel such as the point of highest peak, point of steepest downslope, etc., also through interaction with the GUI. Alternatively, the software executing in the EP system can operate to identify and automatically position (subject to user confirmation or change) the reference channel marker at a location between the region of interest markers 402, 404 so as to coincide with a prescribed signal pattern of interest, including a highest/lowest peak, point of steepest downslope, and any other parameter that can be prescribed. The EP System does this using a conventional algorithm. Thus, in the case of peak detection, a peak within the region of interest is located based on a configuration value that can be preset or reassigned a value in a setup screen of the system. Of course, the prescribed signal pattern can be selected by the operator, with the result being that the operator can have the EP system automatically locate that signal feature between the region of interest markers rather than doing so manually.

By defining a region of interest about a particular heart beat, and by designating a mapping channel and a reference channel, electrophysiologic data can be captured and associated with each channel of the catheter and, likewise, associated with the selected positions on the selected anatomical model. The map module can be utilized in real-time throughout the course of an EP procedure, that is, to show single-beat updates to the EP data, map and calculations, or retrospectively in a review mode.

Referring now to Block 106 a user selects the map mode such as by interacting with tab or control 210 which calls up a map display 300. The map display includes controls suitable for generating a variety of different maps on the basis of the captured electrophysiologic data.

Figure 3:
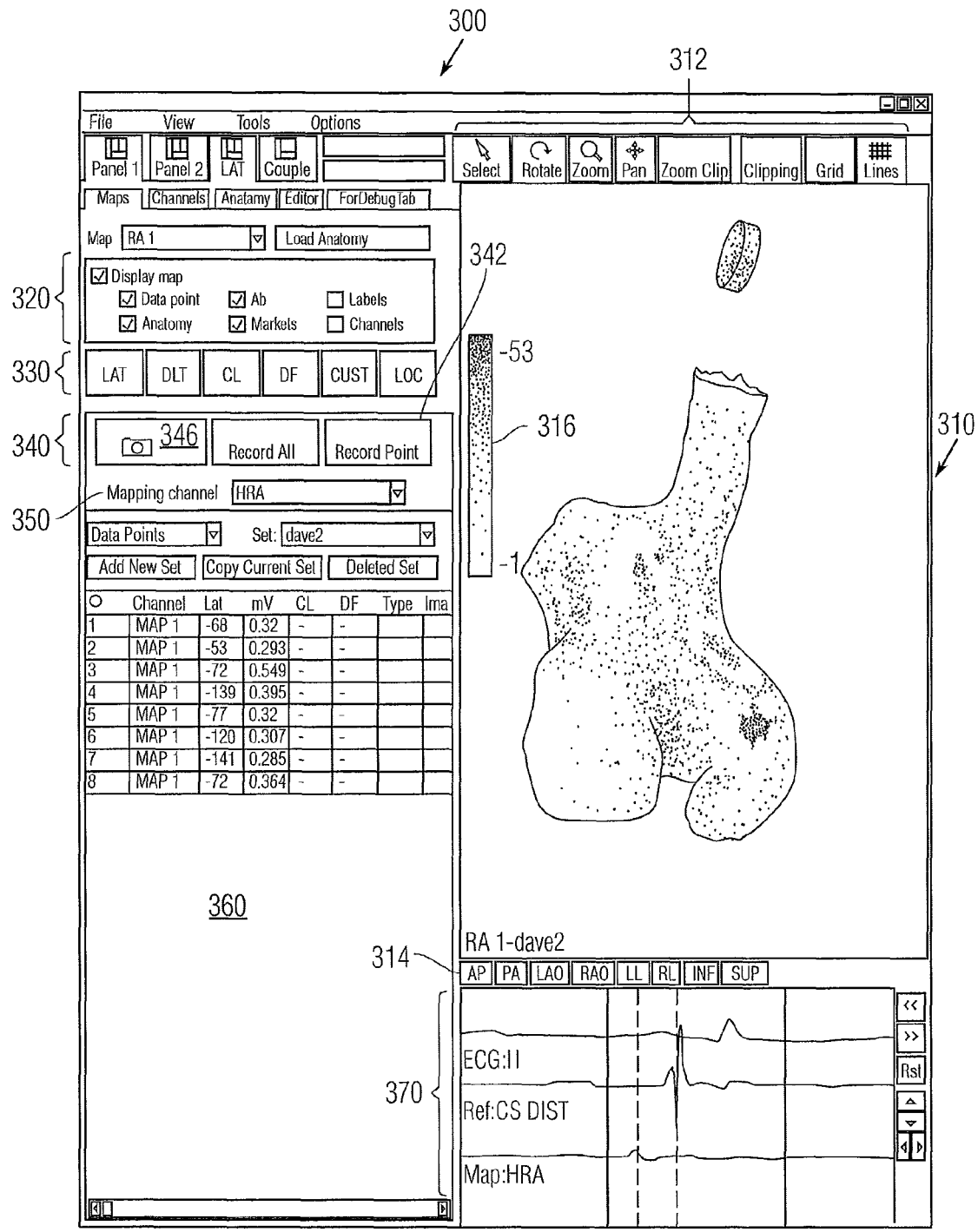
FIG. 3 illustrates an embodiment of certain panels that can be provided by the user interface for mapping EP data that has been acquired sequentially onto a 3D anatomical model and for managing such data.

FIG. 3 illustrates a map display window 300 which an operator can use to generate a three dimensional map of the cardiac data. The map display window 300 contains menus, toolbars, a control panel and views that allow the user to perform many functions including the loading of CT geometries and manipulating one or two heart chamber views (e.g., Zoom, Rotate), locating channel positions upon which multiple forms of analysis are done, displaying a "map" with the resultant analysis data in tabular format (the results data grid 362), displaying waveforms for analysis channels related to the resultant analysis data (e.g., the LAT window 370), and configuring map templates (e.g., Channel positions, electrically passive areas) as discussed with regard to FIG. 2.

At any given time a three dimensional map can be displayed within a panel 310 and can be rotatable, zoomable, and otherwise manipulable through a variety of controls 312. Each of these controls can be selected using a conventional mouse or other input device. Maps can be displayed from a variety perspectives such an anterior posterior, posterior anterior, left anterior, oblique right anterior, oblique, left lateral, right lateral, inferior, superior, using controls 314. The features that are displayed on a given map can vary and can be selected or deselected by a user through control box 320. Using the check boxes within control box 320, the user can elect not to display map at all or if a map is to be displayed, the user can include or exclude the data points themselves (to thereby show only the interpolated data), the ablation sites if any, labels, and the anatomy (meaning that the data points can be displayed without the underlying model being displayed), markers, and the actual channels that are being mapped. In FIG. 3, the map is a local activation time map, but the map module can generate a variety of other maps, including a voltage map (indicative of health of tissue) a cycle length map, a dominant frequency map, a map of custom parameters (e.g., a correlation map, a temperature map, an impedance map, etc.).

Also, plural map panels 310 can be displayed, such as two panels. This permits pre- and post-ablation maps to be displayed along side one another for physician review. The software can link plural maps to each other or to underlying data in the results data grid 362.

A color coding is applied to the map which depicts variations in activation time or any other parameter being mapped in accordance with a color scale. A color scale 316 can assign a color to each data point in the range of calculated values. The values used for assigning the color range can be, for example, the minimum and maximum values within the results data grid 362 of the event log 360. Thus, with respect to the activation time calculations shown in FIG. 3, the earliest activation time is assigned red and the latest activation time blue, with those colors applied to the spheres at the location of the respective measurements and a spectrum of colors on the color scale 316 interpolated across the cardiac model between the measurement locations. In a conventional manner, an ectopic focus can be displayed in red.

The map display 300 has several panels which cooperate to provide the user with an interactive map creation experience. Panel 310, displays a three dimensional map, while panel 320 provides the user with controls over the manner in which the map is displayed. Panel 330 provides selection buttons so that the user can vary the type of map which is to be created. Controls 340 impact the type and amount of data that is captured during the course of an EP procedure. Selection list 350 enables the user to select different channels for any given map, and in this regard, it should be noted that the map displayed in panel 310 concerns a single active channel (the mapping channel). Of central interest, however, is an event log 360 which maintains the data useful in constructing maps and synchronizing the LS Pro or other EP system that may be used with the mapping module. Synchronization of the map module windows/panels with the EP system can be achieved by double-clicking, for example, on a row in the event log or on a data point on the map or on a point on the electrogram.

The event log is populated in response to the user recording data during the course of the EP procedure. In part, the event log is a visual display of the contents of a data structure that manages the information associated with each channel, on an event-by-event basis. The data structure can be organized by channel, and each channel can have multiple records—one for each event. A given record, therefore, identifies a channel, the event number, fundamental information captured from an electrode such as a voltage, temperature, or impedance, a recording time at which the event was logged, calculated values (such as local activation-times, dominant frequency, cycle length, etc.), the color accorded to a given channel on the EP system display (so that the mapping module depicts electrograms for each channel in the same color as used by the EP system), any fluoroscopic image that is associated with that channel at that recording time, the position on the anatomical model at which the channel has been associated, and potentially other information. Through the exchange of messages between the Lab System (or other EP System) and the map module, which include the contents of a data structure such as described above, the map views, ECG waveform, and event data can be mutually synchronized and responsive to user selections with the display of any of this information to coordinate the display of the other views. In other words, if the operator scrolls through the timeline of the ECG waveform within the LAT view 370 and selects an event of interest on a given channel, the values on the other channels will be brought into view in the grid 362 and the map in panel 310 will depict the calculated values for the locations selected for that moment in time. If the operator then selects a different channel as the active channel for that same point in time, the LAT view 370 will update to synchronize with that selection.

The data in each event log entry can be displayed in one or more different maps. Thus, the activation time is displayed in an activation map and the cycle length data is displayed in a map of cycle lengths. The operator can move a current data point, whether it is recorded data captured by the EP system and sent to the map module as a message or whether it is a perceived position of an ablation site or an anatomical marker. A right-click within the 3D view, for example, can provide the user with such control through the user interface.

A variety of anatomical markers can be selected through a dialog box or other user-interface construct. These markers can be pre-defined, such as:

| LSPV(*) | RSPV(*) | LIPV(*) | RIPV |
| --- | --- | --- | --- |
| SVC | IVC | TA | MA |
| Aort.Ann. | Pulm.Ann. | HIS | CS(*) |
| Mcv | Appendage | Bach.Bund. | Fosa |
| SA Node | AV Node | Term.Crest. | Inferior.isth. |
| Septal.isth. | Ref.Chan. | | |

The map display 300 further includes a panel 370 that provides a dedicated display of local activation time (or another parameter of interest), together with the relevant markers. The markers in the LAT display, in the results data grid, and in the map are all linked so that any change on the EP system causes corresponding updates to the markers, and vice versa. The LAT window displays a number of the waveform points across the region of interest and on either side thereof for the selected mapping channel, reference channel, and ECG channel. The number to be displayed is configurable, and all of the markers and electrograms across each channel (e.g., all active channels on the LS Pro) can be presented in individual LAT displays. Controls are provided to stretch the horizontal (time) axis, to zoom the amplitude, to scroll to earlier or later beats, and to reset to the default user configuration.

The events in the event log, and the data contained therein, are what transform an anatomical model of the heart into a three dimensional map of the cardiac data of a given EP procedure. The mapping module of the present invention generates a three dimensional cardiac map with regard to assigned positions of the available channels, and not with regard to actual position of any electrode within or upon a patient. As a result, the channels can be repositioned, if desired, or as a result of roving a mapping catheter, without regard to its actual position, yet still produce a three dimensional cardiac map. The way in which this is achieved, in accordance with a salient aspect of the present invention, is best understood with further reference to FIGS. 1 and 3.

At block 108 of FIG. 1, an operator pilots a catheter under fluoroscopic guidance to locations within the patient's cardiac chamber under investigation. At intervals, a fluoroscopic image is displayed on a fluoroscope which reveals the present location of a catheter relative to the patient's anatomy. Using the operator's skill and experience, that general position can be identified within the template selected during the setup process (Block 104) and the location indicated on the cardiac template. Optionally, the physician can call out a grid position that identifies in two-dimensions the location of the electrode for the module operator to note on a grid overlay of the template. In this regard, the physician and the map-module operator can view the same screen or two screens showing the same information so that the operator can more accurately record the location selected by the physician. In any event, the location is indicated by clicking on the map. By clicking on the map, a new location is associated with the template, but no data has yet to be captured. The operator can record the point using control 342 (or control 344 described below). A message is then sent from the map module to the EP system requesting the cardiac data for the selected positions at that point in time be provided to the map module for that channel.

Conveniently, the results data grid 362 manages all of the values that populate the various windows and panels of the map module, and so the contents of this data grid can be used to construct messages for sending to the EP system, and the grid has defined fields that are ready to receive field-delimited data from the EP system. Field delimited data is a generally available output of most EP systems, including the LS Pro, so that the data can be exported from the EP system and imported into other software packages.

Also optionally, a fluoroscopic overlay can be provided over the map panel 310 with the same scale, magnification and orientation as the segmented model to provide a manual guide as to the actual position of the catheter relative to the segmented model, or to provide an automated determination of position of the catheter relative to the segmented model. The manual guide has the operator confirming each electrode location within the segmented model whereas the automated guide has the software performing the confirmations automatically by matching the darkened portions of the image (where the radiopaque electrodes are located) with positions within the segmented model. Of course, a hybrid approach can propose the positions to the operator with the operator making the final determination as to whether to accept the positions into the model. This approach can improve accuracy as compared to relying on a perceived location, and can be achieved free of sensors to track the location and orientation of any or all electrodes. The operator then records the point or points using controls 342, 344. A message is then sent from the map module to the EP system requesting the cardiac data for the selected positions at that point in time be provided to the map module for that channel. Thus, in this example, a single location on the map has been selected as corresponding to a particular fluoroscopic location, as indicated at block 110. As indicated at block 112, the operator instructs the map module to record the data point associated with that channel, which is done by interacting with control 342. The EP data is transferred from the LS Pro or other EP system to the map module, which in turn performs calculations such as the activation time, the cycle length, the dominant frequency, etc., as indicated at block 114. Cycle length can be calculated as described in co-pending U.S. patent application Ser. No. 11/120,633, entitled "High Density Atrial Fibrillation Cycle Length (AFCL) Detection And Mapping System," filed on May 2, 2005, which is hereby incorporated by reference in its entirety. The data received from the EP system, and each of the calculations that is to be performed, are populated within the event log 360. It should be noted, that to minimize burdens on the processor executing the map module, only those calculations that are necessary for the selected map need to be performed at any given time, but they preferentially can be done in advance so that the user can rapidly switch between maps of Activation Time, Voltage and DF. Each map is created by applying a respective, suitable signal processing algorithm (as known in the art) to the data associated with the selected set of channels (data points on the map). Thus, if activation time is the selected map type (as illustrated in FIG. 3), then Fourier analysis need not be done on the data because no frequency calculations are required. Once the calculations are performed, which can occur within a matter of seconds or less, the result of the calculations can be displayed in the event log as indicated at block 116 and the local activation window 370 can be populated with the waveforms associated with the channel under investigation, as indicated at block 118. With further reference to the local activation time ("LAT") window 370, once data has been captured over a region of interest that window can be populated with the waveforms over that interval, as well as indicators which correspond to a reference channel marker and the mapping channel marker, the difference defining the activation time at the current location of the mapping catheter.

As noted, the event log is updated with the calculations that have been performed as well as the data received from the EP system, as indicated at block 120. In addition, the activation time that has been calculated is placed onto the map. Preferably, the data points that are added to the map comprise color indicators, and more preferably compressed color spheres, which at least partially project from the surface of the map in order to provide a visual indication as to where the data was captured, as opposed to data that has been interpolated. Once at least three data points have been so captured by performing blocks 112 through 120, the surface of the cardiac model can be interpolated and a three-dimensional continuous color changing map can be rendered, as indicated at block 122.

The size of the measurement spheres that is depicted on the segmented model is user configurable and can be changed to emphasize to the user the difference between measurement positions and interpolated data.

Interpolation of the data is performed with regard to electrically active areas of the model. Interpolation is invoked whenever a data point is recorded once there are three or more data points in the results data grid. Interpolation is also invoked whenever a data point reference position or roving position is adjusted in the LAT window 370, or in a similar waveform window showing a different parameter. In both of these cases the three main types of analysis data are interpolated, namely, LAT, voltage and dominant frequency. Custom and cycle length analyses can be interpolated if there is data in the associated column of the current results data grid 362.

Figure 5:
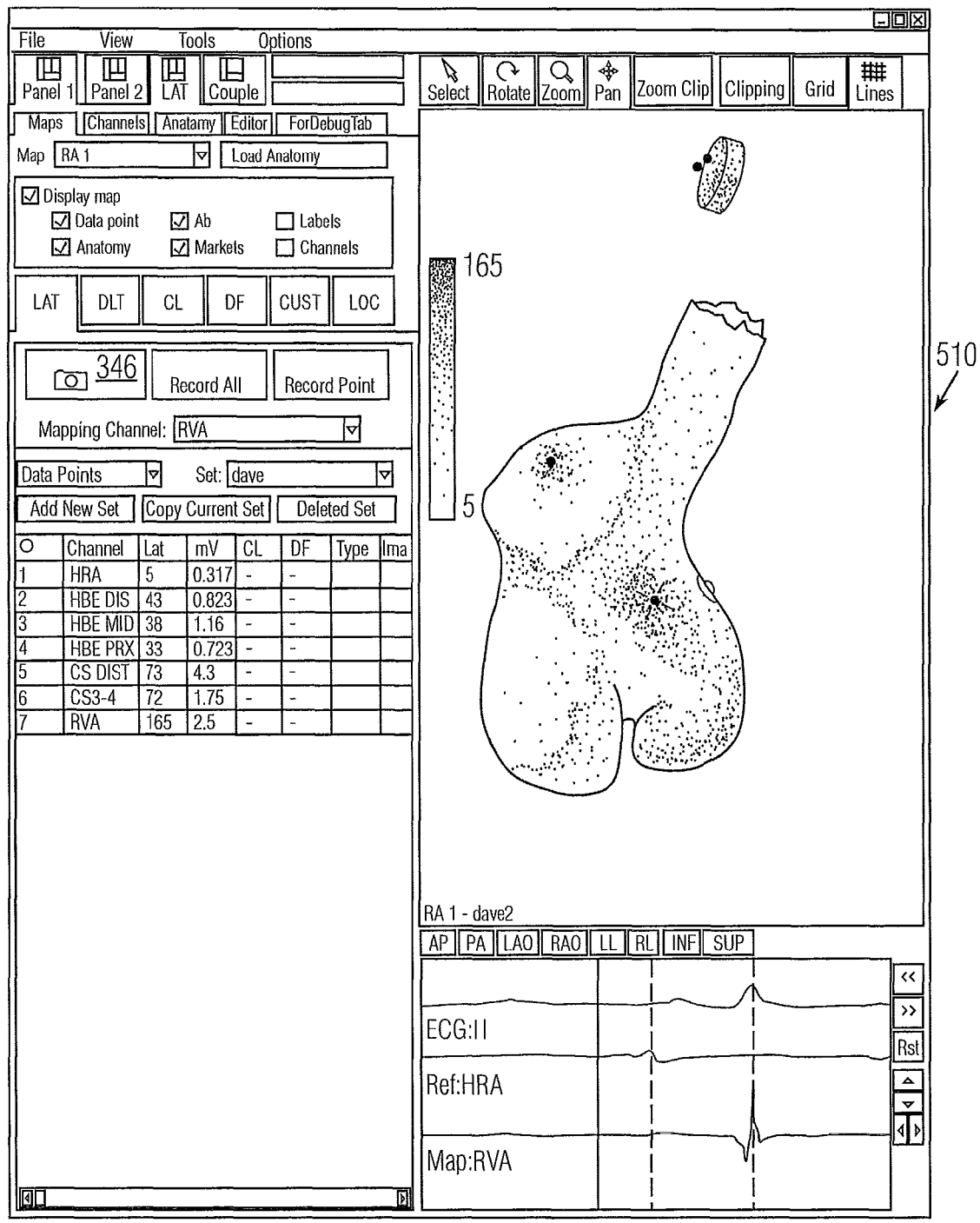
FIG. 5 illustrates an optional feature in which the opacity of the 3D map increases at locations that include mapped EP data.

If a template is used, one or more neutral areas can be identified as tissue not subject to data interpolation. For example, the segmented model can include a portion of the arch of the aorta which can be isolated from the electrically active area by a boundary zone. The boundary zone can be part of the template's definition, and can be re-defined by the user, as desired, by paint or dragging operations using a mouse or other input device. In a similar way, a chamber can be excluded from interpolation by defining a boundary zone so as to exclude it from other tissue in the cardiac model. Any boundary zone so defined can be saved, regardless of whether the model was a template from a library or the patient's own cardiac CT image. As noted above, a user may prefer to view the data points without the anatomical model overlay. This may be advantageous in situations in which the clinician wishes to see precisely where data has been collected, and not have that information obscured by the interpolation. The interpolation process results in a continuously changing color pattern across the surface of the anatomical model which provides insight to the clinician as to the location of the earliest activation time, locations of necrosed or diseased tissue, indications of an aberrant cycle length, and the like. However, there are situations in which it is preferable to remove the anatomy from the display, if only to observe where data has been collected already. To further assist the clinician in identifying those locations where it may be desirable to collect additional information, and in accordance with a further aspect of the invention, the activation map (or any other map being created) can be rendered in a semi transparent mode. This allows the user to see through to the inside of the heart and preferably increases in opacity in those regions in which there has been a high density of data points collected and to remain transparent in regions where there are few or no data points. In this way, the user is provided with a qualitative perspective on how reliable or accurate the interpolation is in any given area. This is illustrated in FIG. 5 in which the panel 510 is substantially the same as panel 310, except the semi-transparent mode has been enabled. As a corollary, then, it should be understood that the opacity at locations that include mapped EP data is greater than the opacity at locations that do not include any or as much EP data mapping.

Referring again to FIG. 1, the calculations performed by the map module include, among other things, the application of raw data collected from the electrodes (which correspond to each channel under investigation) to the waveforms in order to arrive at various calculations such as activation time. In connection with the use of these algorithms, an exact location of the marker on the reference channel is identified by the algorithm for use in the calculations. This refinement in the marker location for the reference channel, as well as the calculations that were made on the data by the map module, is provided to the EP system in an electronic message, as indicated at block 124. As a result, the EP system is provided with the calculations performed by the map module as displayed in the event log 360, in the local activation time window 370 and in the map pane 310. As can be seen in FIG. 4, one or more activation time callouts are illustrated in conjunction with respective active channel to inform the clinician of the activation time of the active (mapping) channel as compared to the other active channels. Thus, in FIG. 4, the mapping channel is HRA and has activation time of 5 milliseconds as compared to the other channels under investigation which have activation times of 33-73 milliseconds, all relative to the reference channel marker. As will be understood by those of ordinary skill in the art, this indicates that the present location of the roving catheter HRA is comparatively close to the earliest activation time that has been identified, so far, and therefore indicative of the situs of the cardiac arrhythmia.

The clinician may wish to continue moving the mapping catheter about the cardiac chamber under investigation in order to find additional or better or different data about the heart's response to its natural cycle, or in response to a pacing electrode (not shown). Thus, at block 126 a test is made to determine whether to repeat the mapping steps for an additional channel, which for purposes of this disclosure includes repeating the mapping steps for the same channel. In a manual mode of operation, the clinician can continue the process by piloting the catheter to a new location within the cardiac chamber, again under fluoroscopic guidance as indicated in block 108) and then repeat steps 110-124 in order to capture additional electrophysiologic data, perform desired calculations on that data such as calculation of activation time, and to update the map in panel 310 and the event log in panel 360 and the local activation time window in panel 370 and to annotate the electrogram signals in the EP system through messages passed between the map module and the EP system.

Figure 6:
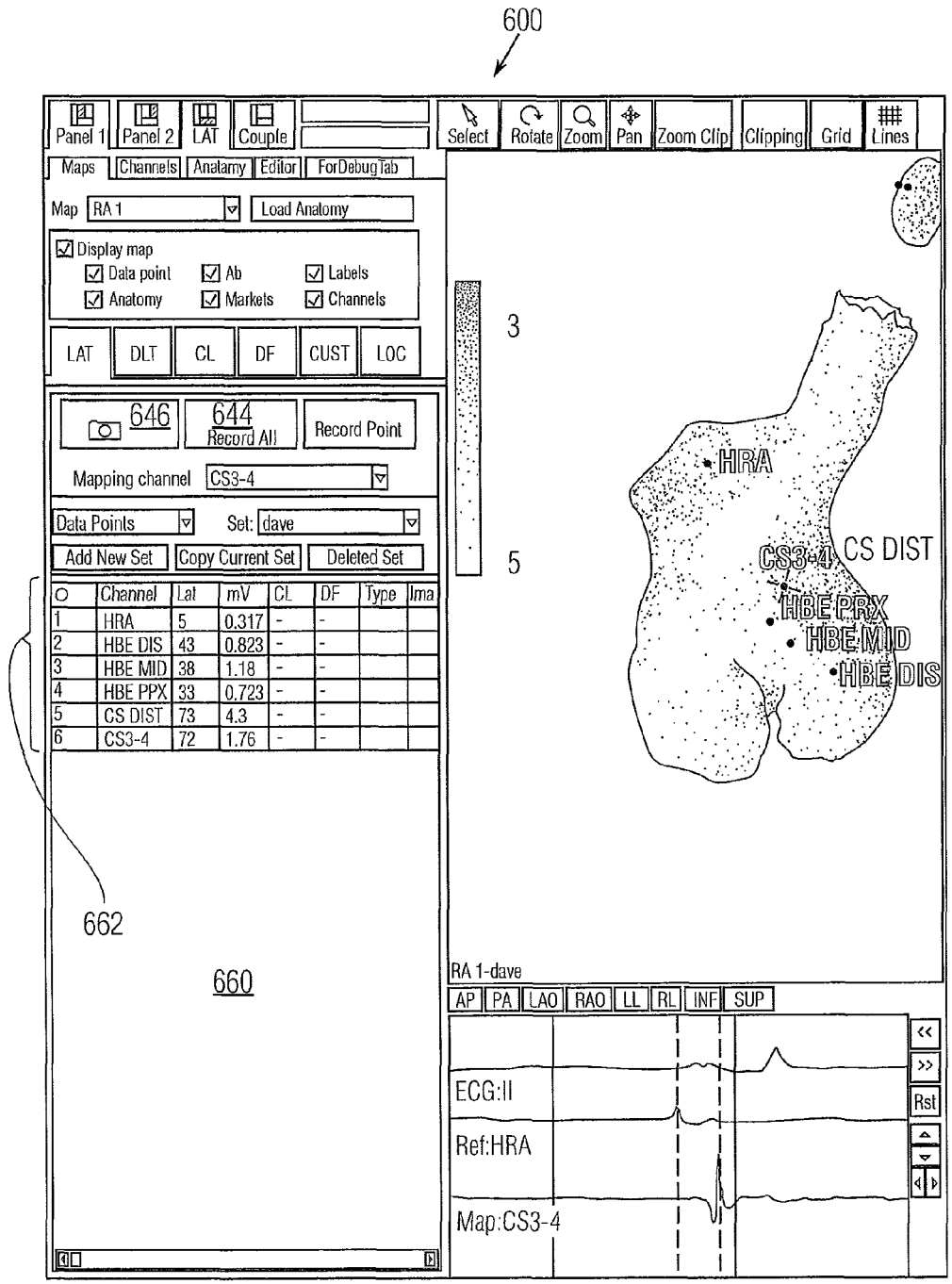
FIG. 6 illustrates the panels of FIG. 3, and now shows an optional mapping of EP data that has been acquired from a multi-pole electrode onto a 3D anatomical model and an interface for managing such data.

The foregoing steps can easily be repeated in an automated manner when a multipole catheter is being used. Referring briefly to FIG. 6, a multi-channel catheter has several active channels on the cardiac template and electrophysiologic data for each of those channels can be captured by the foregoing steps and a signal recording time by selecting the "record all" control 644 shown in the map display 600. The record-all control is similar to the record-point control except that it causes the process to be iteratively performed until each of the active channels has its data captured, calculations performed, and updates to the respective windows, maps, event logs and electrograms, as previously described. It should be understood, however, that while the record-all control enables data to be acquired from the active channels all at the same time, the calculations and updating of display follow one another in time. Nevertheless, all of the foregoing steps can be performed in a matter of seconds or less.

Once the clinician is satisfied that sufficient data has been gathered to construct a map—including a sequentially obtained map as described with regard to FIG. 3 or a multi-channel map as described in connection with FIG. 6 or a composite map which is a hybrid of both single point and multi channel acquisitions—then the clinician can consider performing a treatment on the heart to overcome its ailment.

For example, the treatment can be an operation in order to eliminate or reduce an arrhythmia. The semi-transparent mode can be actuated to satisfy the clinician that he has gathered sufficient data within the region at which the focus appears to be located.

It will be appreciated that a composite map includes single-beat multichannel data and single channel data from different cardiac beats. A composite map can result from the use of a multi-electrode catheter for rapid data acquisition in a single beat followed by a point-by-point mapping to fill-in areas of interest.

Throughout the progress of the EP procedure, the map module of the present invention can provide further functionality to assist the clinician in mapping and treating heart problems. For example, control 346 and 646 illustrated in FIGS. 3 and 6, respectively, can be used to capture an image at the particular location of the mapping catheter at the time a particular event is taking place. For instance, the image being captured can be a fluoroscopic image. The fluoroscopic image is not only captured, but it is stored within the data structure in association with the event number. As a result, each mapped channel can have a fluoroscopic image associated with its position at the time of the event, its electrogram data, as well as the recording time. Likewise, each mapped position on the map itself is associated through the event log 360 with any fluoroscopic image that was captured when the data was captured at that electrode position, such that a user can click on the map and cause the software to recall the associated fluoroscopic image, or click on the event in the event log. Consequently, a physician can retrieve the fluoroscopic image and use it to guide back to a location of interest, or can use this feature during a review mode to more generally coordinate past locations, as identified by the captured fluoroscopic image, with specific waveform electrogram sets across the various channels of investigation and with a 3D image of the electrogram data.

It should be appreciated that the control 346, 646 can associate a fluoroscopic image with the results data grid for coordinated retrieval in relation to the data recorded at the time of the event, and also can associate other data that is captured in association with an event. As non-limiting examples, EP systems can also include ultrasound data capture and other positioning systems that determine the location of an electrode or the catheter, and that information can be stored in association with the electrograms and calculated measurements.

Thus, at block 128, a test is made to determine whether the clinician wishes to capture an image, and if he does then the fluoroscopic image is stored and associated with the event at block 130. Thereafter, tests are made first at block 132 and then at block 134 to ascertain whether there has been manipulation of any of the data at either the map module or the EP system, respectively.

In the event that there has been manipulation of data at the map module, a first test is made at block 136 to determine whether it is a manipulation of only the map itself. The map can be manipulated, for example, by the clinician relocating a channel along the surface of the model. In that case, the data displayed on the map and within the event log 360 is updated so as to re-interpolate and render once again a map in accordance with those changes. If the data manipulation at the map module concerns a change in location of the mapping channel marker or of the reference channel marker, then a message is sent to the EP system in order to synchronize it with such changes made at the map module. The purpose of the synchronization is to ensure that the map module and the EP system are operating under the same underlying parameters and settings. Re-interpolation is performed at block 138 and any messages that are sent to the EP system are done, as indicated at block 140. Continuing, an event that data manipulation has occurred at the EP system, such as the clinician determining that a new region of interest is appropriate, then a message is communicated to the map module, as indicated at block 142, to provide it with the changed parameters. Any message received from the EP system at the map module is processed by updating the contents of the event log. The event log, as noted above, serves as a central repository as the parameters with values and calculations that instruct the creation of the three-dimensional maps in panel 310.

Figure 7:
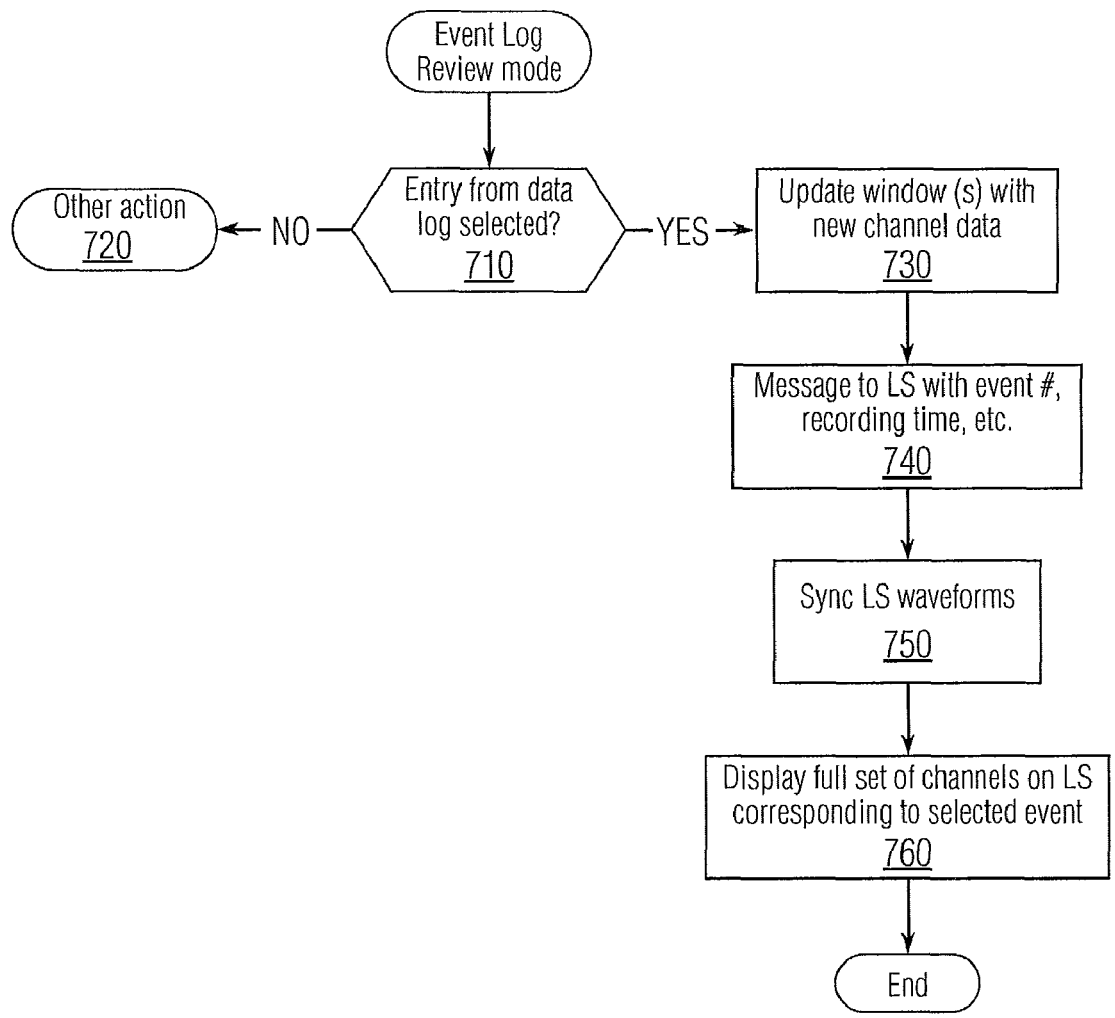
FIG. 7 is a flow diagram illustrating an event log review mode in accordance with a further aspect of the invention.

Referring now to FIG. 7, a review mode is provided in which the clinician or operator can inspect any of the entries within the event log 360. At step 710 a test is made to determine whether data from the event log has been selected. At any time, because the interface is event driven, the user can select a variety of actions including going into a setup mode, rotating or zooming the map image, changing the perspective view of the image or changing the type of map to be displayed and so all such other actions can be handled at block 720. In the event that the user has interacted with one of the entries in the event log, then one or more windows are updated with the selected channel data, as indicated at block 730. In FIG. 3, for example, event No. 1 has been highlighted and the local activation time window 370 shows the selected channel at that point in the electrophysiologic procedure. Upon selecting entry No. 1, a message is conveyed to the EP system with the event number, the recording time and other information such as the dominant frequency (if calculated), as indicated at block 740. The EP system responds to that message as though it was a command received through its user interface and causes the electrograms to be recalled for that recording time. Consequently, the data displayed in the map module and review mode is again synchronized with the data in the EP system, as indicated at block 750.

By synchronizing the EP system with the map module, a full set of all channels on the EP system can be displayed that correspond to the selected event. Thus, comparing the electrograms of FIG. 4 to the local activation time window 370 of FIG. 3, it can be appreciated that the LAT window 370 shows only a portion of the waveform within the region of interest for the mapping channel, its reference channel and one of the ECG channels, whereas the multi-channel display at the EP system shown in FIG. 4 provides the mapping channel in relation to all the other channels available in the procedure. The EP system is able to navigate along the time line of the electrograms and locate the selected event using the information that is provided in the message from the map module t the EP system. That full set of information is displayed on the EP system as indicated at block 760.

Figure 8A:
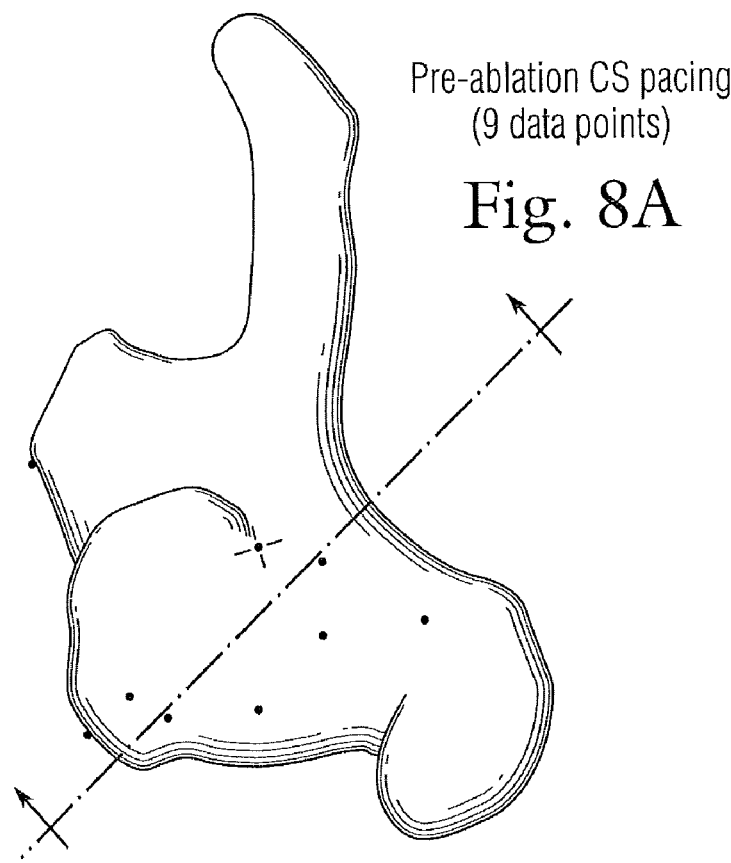
FIGS. 8A and 8B illustrate exemplary 3D maps that are displayable in tandem to assist a clinician in comparing the behavior of pre- and post-operative cardiac tissue.
Figure 8B:
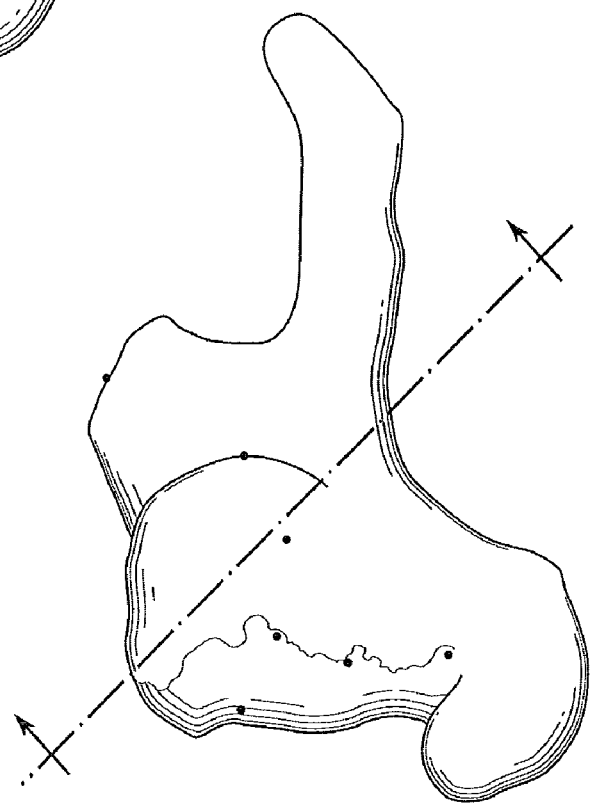

Referring now to FIGS. 8A and 8B, panels 310A and 310B are dual views of the same cardiac model showing different points in time of an EP procedure, namely, pre-ablation and post-ablation views of the heart, respectively. These views can be displayed alongside each other, if desired. These figures also show an orifice that the operator can create using the anatomy editor feature, which can be made available, for example, using a tab or other interactive control provided through the graphical user interface. The orifice is created by painting segments of the anatomical surface. A check box or the like enables the user to select this functionality. Thereafter, a click and drag operation can select a region. The selected region can turn gray, for example. The user can then command the map module to turn the selected region into an orifice, which then appears transparent to permit the operator to see within the chamber. This process is similar to the steps taken to make areas electrically passive (boundaries, scars).

In use, therefore, the operator can position ECG leads within one or more cardiac chambers and set the region-of-interest markers to identify a particular beat on the time-based ECG waveform in the LAT window 370. When data for a point on a given channel or from multiple channels is to be captured, a record control is selected from the map module, and that causes the captured data to be transferred to the EP system as field-delimited data or as a data object by the map module. Likewise, if the operator selects a different channel as the active channel or as the reference, or changes the region-of-interest, etc., messages communicate between the EP system and the map module to ensure that the various views into the underlying data remain synchronized. In part, this enables the operator to navigate the ECG waveform's time line to find an event of interest, and then be able any data recorded on any of the recorded channels at that particular point in time. As such, the invention provides a tool useful for both diagnostic and therapeutic activities.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different points set forth below may be combined various ways in further accordance with the present invention.

We claim:

1. A computer-assisted method for guiding an operator in a placement of indwelling electrodes, including the steps of:
    providing a template model of a heart on a display connected to the computer;
    including a set-up within the display of the template model of the heart, the set-up comprising a pluraltity of locations at which a corresponding plurality of ECG channels are to be associated;
    advancing into the heart a catheter having a proximal end and a distal end that supports multiple electrodes;
    piloting the multiple electrodes into an orientation that generally coincides with the set-up by manipulating the proximal end of the catheter; and
    capturing EP data at the piloted locations onto electrogram channels associated with the respective ones of the multiple electrodes,
    whereby the catheter is navigated free of a precision navigation device.

2. The method of claim 1, including the additional step of confirming that the multiple electrodes on the distal end of the catheter have been guided into the orientation that approximates the set-up.

3. The method of claim 2, wherein the confiming step comprises:
    taking a fluoroscopic image of the catheter after the piloting step, and
    comparing the fluoroscopic image to the set-up displayed within the template model for correspondence.

4. The method of claim 3, wherein the comparing step comprises superimposing the fluoroscopic image onto the display of the template model and the set-up.

5. The method of claim 1, including the additional step of storing a set of data points each having a location that corresponds to a respective location of one of the points in the set-up and a value that corresponds to the EP data on that channel.

6. The method of claim 1, wherein the capturing step comprises transferring electrogram information from each channel of the ECG to a particular point in the set-up that is associated with that channel.

7. The method of claim 1, including the additional step of storing the locations for recall and use in a subsequent procedure.

8. The method of claim 1, including the additional step of selecting a pre-defined set-up for inclusion within the template model of the heart.

9. The method of claim 1, wherein the selecting step is conducted using controls provided on an EP system interface, and wherein a set of points are displayed within the template model of the heart for each pre-defined set-up.

10. The method of claim 1, including the additional step of manually defining the set-up prior to the including step.

11. The method of claim 10, wherein the defining step is conducted using controls provided on an EP system interface, and wherein the operator interacts with the controls to successively establish points for display within the template model.

12. The method of claim 10, including the additional step of dragging one or more of the points to a new location by interacting with the controls.

13. The method of claim 12, wherein the controls comprise a display of channel markers.

14. The method of claim 11, including the additional step of storing the points established by the operator as the set-up.

15. The method of claim 1, wherein the template model of the heart is a segmented model.

16. The method of claim 1, wherein the step of capturing EP data causes portions of the template model to have a first opacity, 17. The method of claim 16, wherein the first opacity at locations that include mapped EP data is greater than a second opacity at locations free of mapped EP data.

18. The method of claim 1, wherein the locations at which mapped EP data are associated are indicated on an iso-parameter map selected from the group consisting of: a local activation time map, a voltage map, a cycle length map, a dominant frequency map, a correlation map, a temperature map, and an impedance map.

* * * * *